US011931518B2

(12) United States Patent
Borsari

(10) Patent No.: US 11,931,518 B2
(45) Date of Patent: Mar. 19, 2024

(54) ACTIVE HUMIDIFIER AND THERMOREGULATED CIRCUIT INTEGRATING SUCH ACTIVE HUMIDIFIER

(71) Applicant: DIMAR S.R.L., Medolla (IT)

(72) Inventor: Maurizio Borsari, Mirandola (IT)

(73) Assignee: DIMAR S.R.L., Medolla (IT)

(*) Notice: Subject to any disclaimer, the term of this patent is extended or adjusted under 35 U.S.C. 154(b) by 574 days.

(21) Appl. No.: 16/975,552

(22) PCT Filed: May 21, 2019

(86) PCT No.: PCT/IB2019/054174
§ 371 (c)(1),
(2) Date: Aug. 25, 2020

(87) PCT Pub. No.: WO2019/224706
PCT Pub. Date: Nov. 28, 2019

(65) Prior Publication Data
US 2021/0069451 A1   Mar. 11, 2021

(30) Foreign Application Priority Data

May 22, 2018 (IT) .......................... 102018000005586

(51) Int. Cl.
*A61M 16/10* (2006.01)
*A61M 16/00* (2006.01)
(Continued)

(52) U.S. Cl.
CPC ........ *A61M 16/109* (2014.02); *A61M 16/024* (2017.08); *A61M 16/06* (2013.01);
(Continued)

(58) Field of Classification Search
CPC .... A61M 16/00; A61M 16/024; A61M 16/06; A61M 16/0833; A61M 16/10;
(Continued)

(56) References Cited

U.S. PATENT DOCUMENTS 4,910,384 A * 3/1990 Silver ................. A61M 16/142
392/503
5,367,604 A   11/1994 Murray
(Continued)

FOREIGN PATENT DOCUMENTS

FR   3 008 319 A3   1/2015
FR   3 013 988 A3   6/2015
(Continued)

OTHER PUBLICATIONS

Davoine et al. Self-Containing Water Tank for Gas Humidifier, Published Jun. 5, 2015. Downloaded Translation by Clarivate Analytics from PE2E on Apr. 17, 2023 and converted to PDF with page and line numbering. (Year: 2023).*
(Continued)

*Primary Examiner* — Joseph D. Boecker
*Assistant Examiner* — Brian T Khong
(74) *Attorney, Agent, or Firm* — Oblon, McClelland, Maier & Neustadt, L.L.P.

(57) ABSTRACT

An active humidifier includes a disposable cartridge provided with a humidification chamber adapted to contain water to be heated for air humidification, with an inlet mouth for air introduced by a ventilation device and with an outlet mouth for conditioned air to a patient, the cartridge includes a disposable heating element directly inserted inside the humidification chamber close to the bottom and distanced therefrom, immersed in the water and lapped on all sides, the cartridge also includes an electrical connector for the electrical connection of the disposable heating element, and the disposable heating element includes an electrical resistor and in the humidification chamber is a sealed casing entirely made of plastic material.

15 Claims, 9 Drawing Sheets

(51) Int. Cl.
*A61M 16/06* (2006.01)
*A61M 16/08* (2006.01)
*A61M 16/16* (2006.01)

(52) U.S. Cl.
CPC .... *A61M 16/0833* (2014.02); *A61M 16/0875* (2013.01); *A61M 16/16* (2013.01); *A61M 2205/0238* (2013.01); *A61M 2205/3368* (2013.01); *A61M 2205/502* (2013.01); *A61M 2230/50* (2013.01)

(58) Field of Classification Search
CPC ............ A61M 16/109; A61M 16/1095; A61M 16/16; A61M 2205/0238; A61M 2205/3368; A61M 2205/502; A61M 2230/50
See application file for complete search history.

(56) References Cited

U.S. PATENT DOCUMENTS

| | | | | |
|---|---|---|---|---|
| 2009/0107980 A1* | 4/2009 | Andel | ................. | A61M 16/109 219/443.1 |
| 2010/0147299 A1 | 6/2010 | Row et al. | | |
| 2012/0255944 A1* | 10/2012 | Zhang | ................... | H05B 3/345 219/494 |
| 2014/0131904 A1* | 5/2014 | Tang | .................... | A61M 16/16 261/157 |
| 2014/0216459 A1* | 8/2014 | Vos | ................... | A61M 16/0057 128/204.17 |
| 2014/0283829 A1* | 9/2014 | Miller | ................. | A61M 16/109 128/203.14 |
| 2014/0352694 A1* | 12/2014 | Row | ..................... | A61M 16/16 128/203.14 |
| 2015/0030317 A1* | 1/2015 | Bayer | ................. | A61M 16/161 261/142 |
| 2016/0228671 A1* | 8/2016 | Jackson | ............. | A61M 16/024 |
| 2018/0250490 A1* | 9/2018 | Burgess | ................ | A61M 16/16 |
| 2018/0250491 A1 | 9/2018 | Row et al. | | |

FOREIGN PATENT DOCUMENTS

| | | | | |
|---|---|---|---|---|
| FR | 3013988 A3 * | 6/2015 | .......... | A61M 16/109 |
| WO | WO 2018/016977 A1 | 1/2018 | | |
| WO | WO-2018016977 A1 * | 1/2018 | ........ | A61M 16/0066 |

OTHER PUBLICATIONS

Merriam-Webster Dictionary, Definition of the verb "Lap", Downloaded to PDF on Apr. 20, 2023. (Year: 2023).*

International Search Report dated Sep. 6, 2019 in PCT/IB2019/054174 filed on May 21, 2019.

* cited by examiner

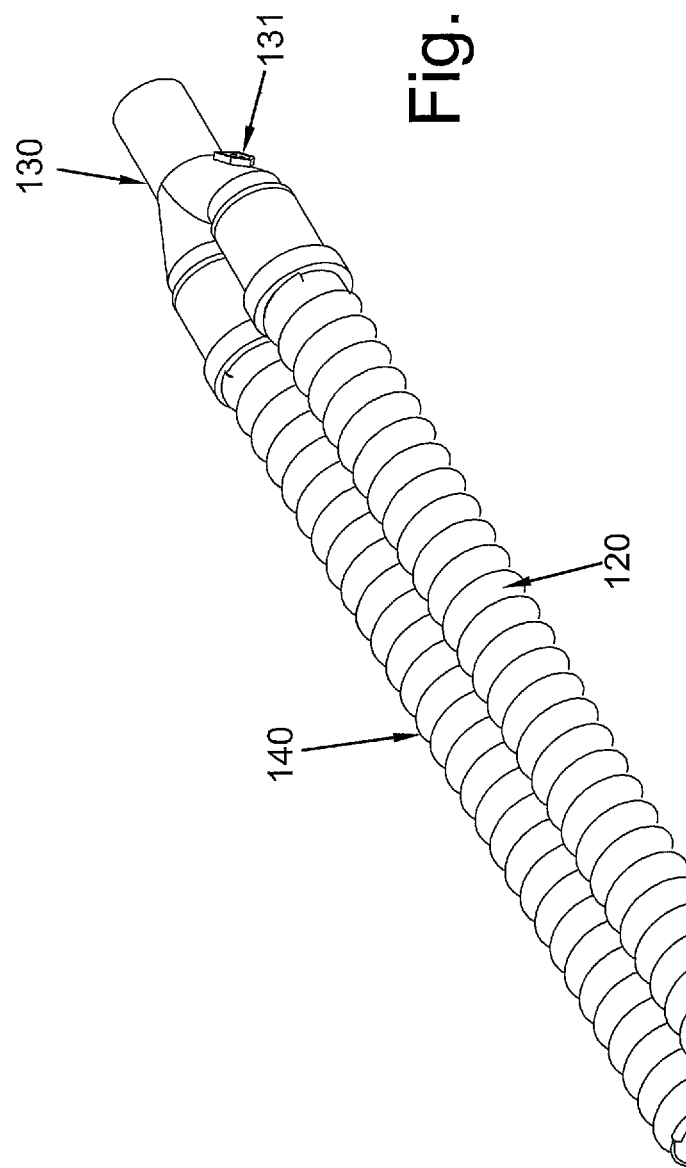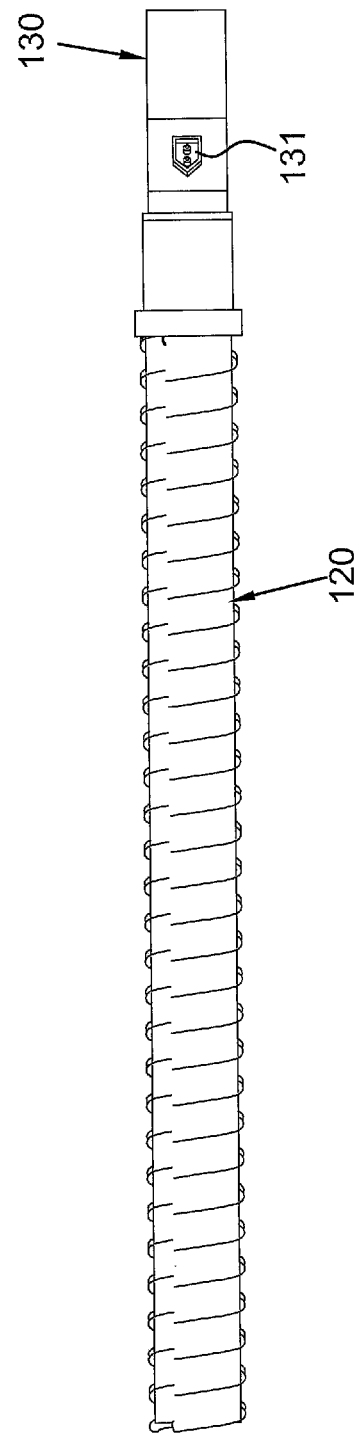

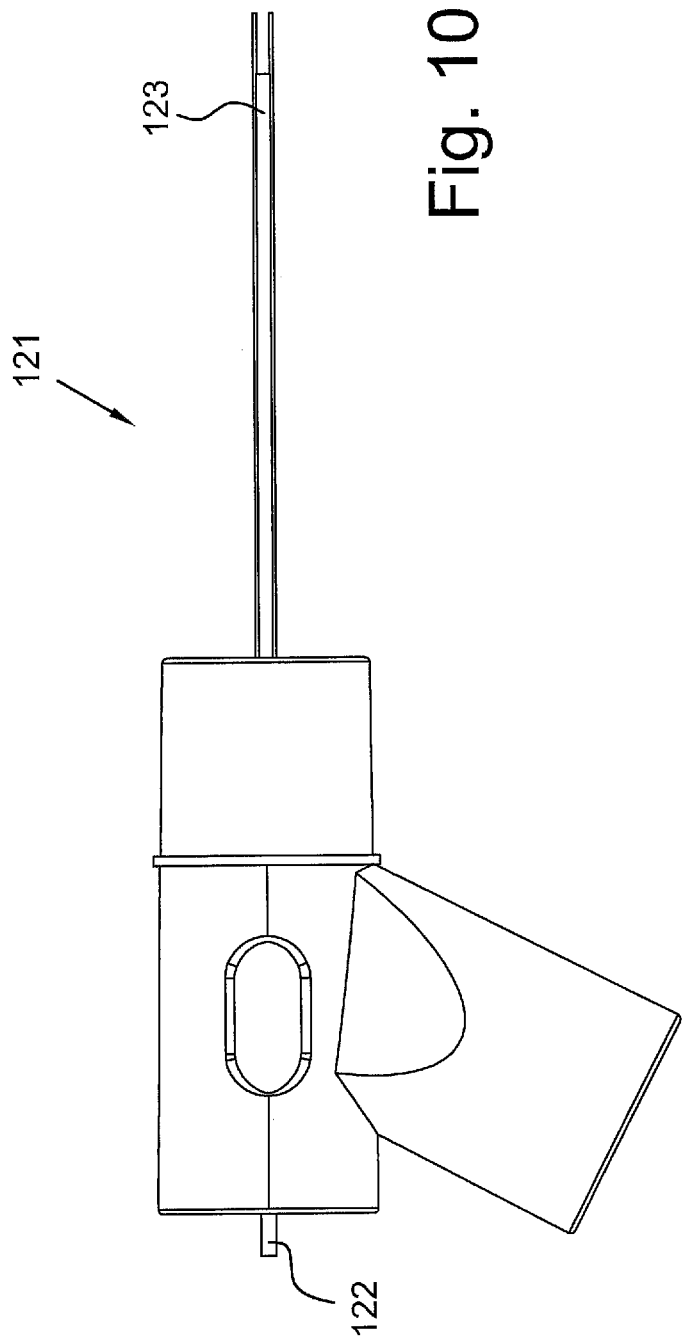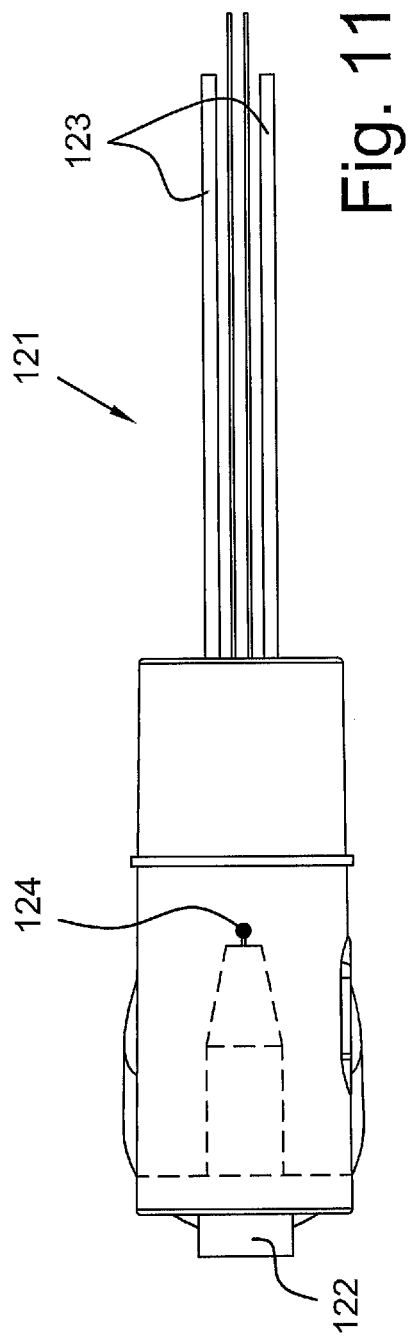

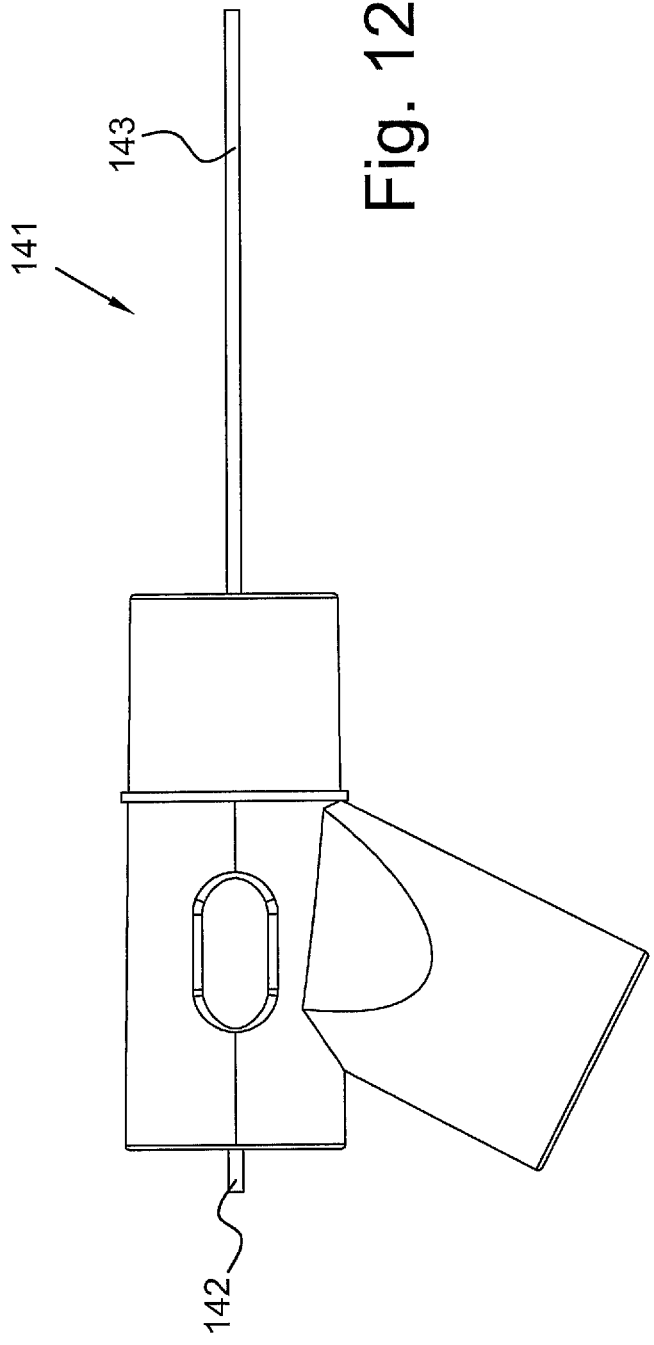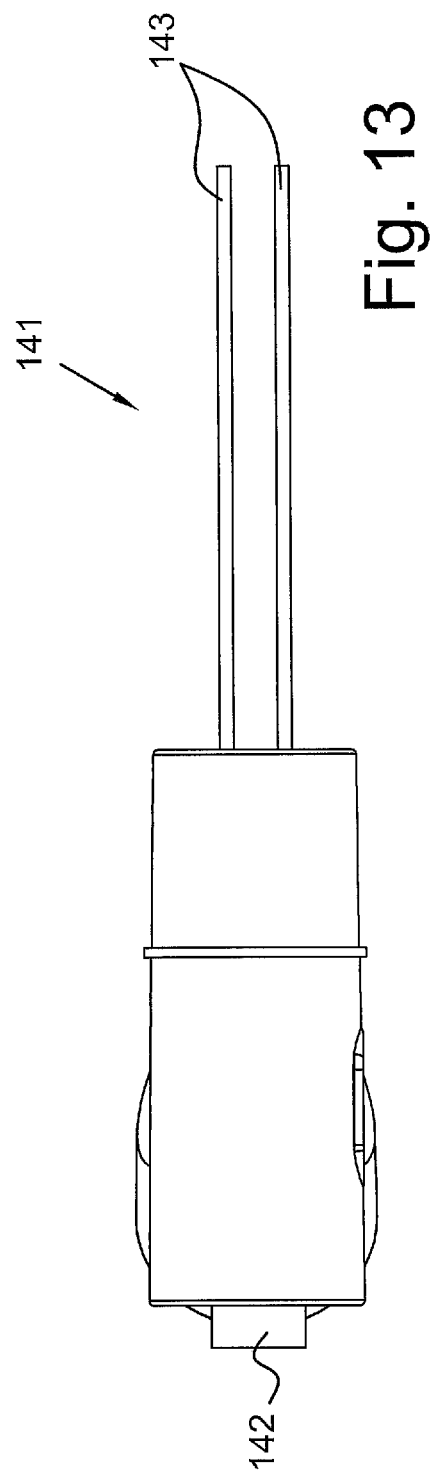

ACTIVE HUMIDIFIER AND THERMOREGULATED CIRCUIT INTEGRATING SUCH ACTIVE HUMIDIFIER

The present invention relates to an active humidifier and to a thermoregulated circuit integrating such active humidifier.

In normal breathing, the upper airways contribute to heat and humidify the inspired air and to retain the heat and the humidity contained in the expired air, then to release them again during the subsequent inspiration.

During inspiration, environmental air is normally heated until reaching, at the level of the branching between the trachea and the bronchi, the "carina", 37° C. and fully saturated at 100% until it contains 44 mg of water per litre of ventilated air.

In invasive mechanical ventilation, the upper airways of the patient are bypassed by the introduction of the tracheal tube. Consequently, the patient's lungs are reached by colder and drier inspired gases with respect to normal breathing without bypass. The normal exchange process (absorption and transfer of heat and humidity by the airways during breathing) is thus missed.

Prolonged exposure of the delicate pulmonary tissues and of the mucociliary epithelium to improperly conditioned ventilation gases can cause numerous problems, such as localised inflammation of the trachea, reduction of the cilia function, retention and thickening of secretions, lowering of the patient's body temperature, reduction of the cardiopulmonary function, increased risks of occlusion of the tracheal tube.

This drawbacks are remedied by preventively humidifying and heating the gases inspired by the patient.

Existing heating systems, traditionally used to condition the inspiratory gases, known as active humidifiers, all consists of a reusable electrical appliance containing all electric power systems and electronic temperature control systems and user interface and of a disposable system for channeling and conditioning the respiratory gases, consisting of a circuit of tubes and of a usually disposable chamber for containing the water to be heated, the so-called cartridge, in turn formed by a body made of plastic material having at least one metallic surface, usually made of aluminium.

A permanent electrical resistor contained in the reusable body of the active humidifier heats a temperature conducting metal element, usually made of steel, which is placed in contact with the metal surface of the disposable cartridge, positioned to rest thereon. The water contained in the disposable cartridge is then heated through the metal surface with which it is in direct contact.

The water heats and humidifies the residual volume of air contained in the disposable cartridge so that the inspiratory gases that traverse the disposable cartridge, which can be both alternating and constant, are channeled by the circuit, heated and humidified drawing the volume of residual gas already present in the cartridge itself and sent to the patient.

A series of temperature sensors positioned at the output of the disposable cartridge and at the end of the inspiratory tube, control the value of the temperature of the inspiratory gases and, consequently, regulate the value of energy which the electrical resistor immersed in the heating element supplies to the surface of the disposable cartridge to heat the water contained therein, which in turn transfers heat and humidity to the gases that traverse it, trying to maintain the value of temperature of the aforesaid gases at the value pre-set by the operator on the active humidifier.

In practice, the operator sets the desired temperature of the inspiratory gases on the active humidifier; the reusable electrical resistor contained in the active humidifier heats the reusable metallic element with which it is in contact; the metallic element of the active humidifier transfers by conduction the thermal energy to the metallic surface of the disposable cartridge; the metallic surface of the disposable cartridge is heated by the metallic element of the active humidifier; the heated metallic surface of the disposable cartridge in turn transfers, also by conduction, the thermal energy to the water contained in the cartridge; the hot water contained in the disposable cartridge transfers temperature and humidity to the residual volume of gas present in the cartridge itself; the tubes that channel the respiratory gases carry the cool, dry air coming from a source positioned upstream of the cartridge inside the cartridge itself; the water heated in the cartridge transfers temperature and humidity to the inspiratory gases that traverse it; the inspiratory gases, traversing the heated disposable cartridge, are then loaded with temperature and humidity, being conditioned to the value pre-set on the active humidifier; exiting from the disposable heating cartridge, the inspiratory gases are channeled to the patient; the temperature sensors positioned at the output of the disposable heating cartridge and in proximity to the respiratory tract of the patient, control the temperature values of the gases in order to reach and maintain the values set on the active humidifier.

Therefore, known active humidifiers are based on six heat conduction steps, in particular between the reusable electrical resistor and the reusable metallic element; between the metallic surface of the disposable cartridge and the water contained in the disposable cartridge; between the volume of residual gas in the disposable cartridge and the inspiratory gases that traverse the disposable cartridge.

Therefore, in known systems, the presence of multiple steps of transmissions-conductions of thermal energy, presents a series of problems, including the time required for the inspiratory gases to reach the set value of temperature and humidity; latency and the thermal flywheel once the set temperature value is reached; the "pendulum" effect of the various temperatures both to maintain the pre-set value and with changes in respiratory flows, which can be both alternating and constant, with different characteristics and performances of the active humidifier and related controls; the high quantity of electricity necessary to heat the entire system.

Moreover, in known active humidifiers, the expiratory gases coming from the patient can be subject to condensation during their exit path during which they are cooled. Therefore, it is necessary to manage this condensation because it could be contaminated by pathogenic microorganisms and create contamination conditions that are dangerous for the patient itself.

The aim of the present invention is to provide an active humidifier and a thermoregulated circuit integrating said active humidifier that solve the technical problems indicated above.

Another aim of the present invention is to provide an active humidifier and a thermoregulated circuit integrating said active humidifier in which the electrical connections are made in a rapid and simple manner for the operators.

An additional aim of the present invention is to provide an active humidifier and a thermoregulated circuit integrating said active humidifier that can be directly interfaced at the input with a probe for measuring the patient's body temperature.

Another aim of the present invention is to provide an active humidifier and a thermoregulated circuit integrating said active humidifier that are particularly simple and functional, with low costs.

These aims according to the present invention are achieved by making an active humidifier as set forth in claim 1.

Further features of the active humidifier and of the thermoregulated circuit integrating said active humidifier are set forth in the dependent claims.

The features and advantages of an active humidifier and of a thermoregulated circuit integrating said active humidifier according to the present invention will be more readily apparent from the following exemplifying and non-limiting description, referred to the schematic accompanying drawings, wherein.

Figure 7:
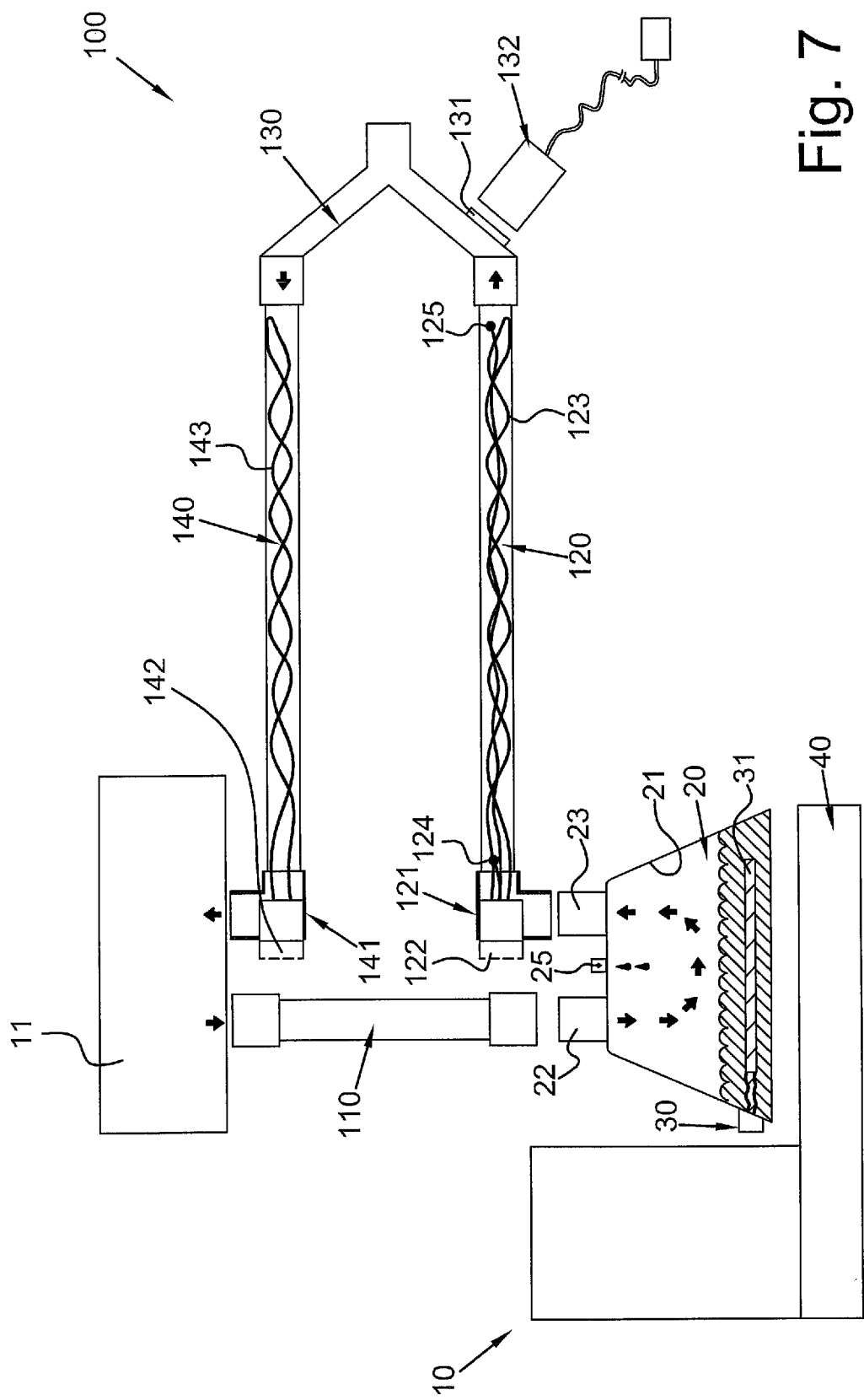

FIG. 7 schematically shows a thermoregulated circuit integrating the active humidifier according to the invention;

FIGS. 8 and 9 are respectively a perspective view and a lateral view of the set consisting of the inspiration tube, of the expiration tube and of the respiratory interface Y-fitting of the circuit of FIG. 7;

FIGS. 10 and 11 are respectively a lateral elevation view and a plan view of a first fitting of the circuit of FIG. 7 for the inspiration tube, integrating an electrical connector for an electrical resistor, for two thermistors and for the connector for the connection of a patient temperature probe;

FIGS. 12 and 13 are respectively a lateral elevation view and a plan view of a second fitting of the circuit of FIG. 7 for the expiration tube, integrating an electrical connector for an electrical resistor.

With reference to the figures, an active humidifier is shown, indicated in its entirety by the numeral 10, along with a thermoregulated circuit indicated in its entirety by the numeral 100, integrating said active humidifier 10.

The active humidifier 10 comprises a disposable cartridge 20 comprising a humidification chamber 21 able to contain water to be heated for the humidification of the air, an inlet mouth 22 for air introduced by a ventilation device 11 and with an outlet mouth 23 for conditioned air to a patient.

The cartridge 20 comprises a disposable heating element 30 directly inserted inside the chamber 21 close to the bottom, immersed in the water contained in the cartridge itself and lapped on all sides. The disposable heating element 30 is, in the example, positioned on a plurality of support pegs 24, which keep it distanced from the bottom.

The disposable heating element 30 is, in the example, positioned on a plurality of support pegs 24, which keep it distanced from the bottom for the purpose of facilitating the convective motion of the water molecules positioned on the bottom of the chamber 21 and in contact with the lower heating surface which, being hotter because:

the volume/mass of water to be heated is smaller, for equal heating surface, than the volume present in the upper part of the heating surface;

they are not lapped by the flow of cold gas entering the chamber 21, rise to the surface passing beyond the disposable heating element 30 mixing itself to the volume of water present in the upper part, raising its temperature and allowing better conditioning (heating and humidification) of the gas flow.

The disposable heating element 30 consists of a disposable electrical resistor 31, preferably having planar development substantially equal to the diameter of chamber 21.

Figure 1:
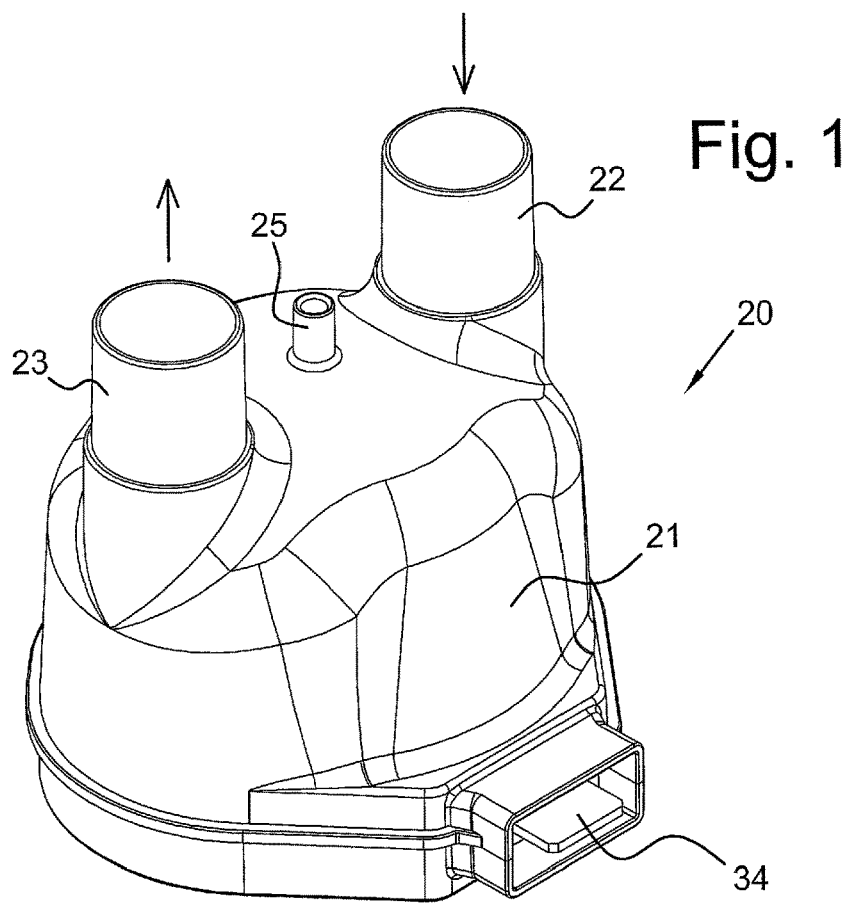
FIG. 1 is a perspective view of a cartridge of the active humidifier according to the invention.
Figure 2:
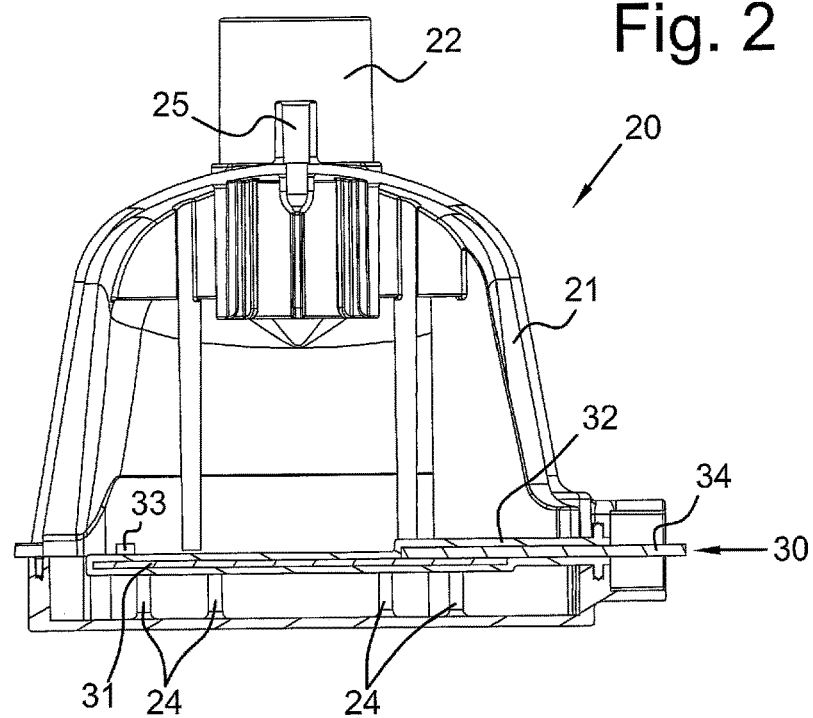
FIG. 2 is a section according to a median plane of symmetry of the cartridge of FIG. 1.

The electrical resistor 31, shown schematically in the section of FIG. 2 as a planar element, preferably consists of a metallic wire wound in a spiral covered by a thin layer of plastic material, such as silicone, not shown in the figures.

Figure 3A:
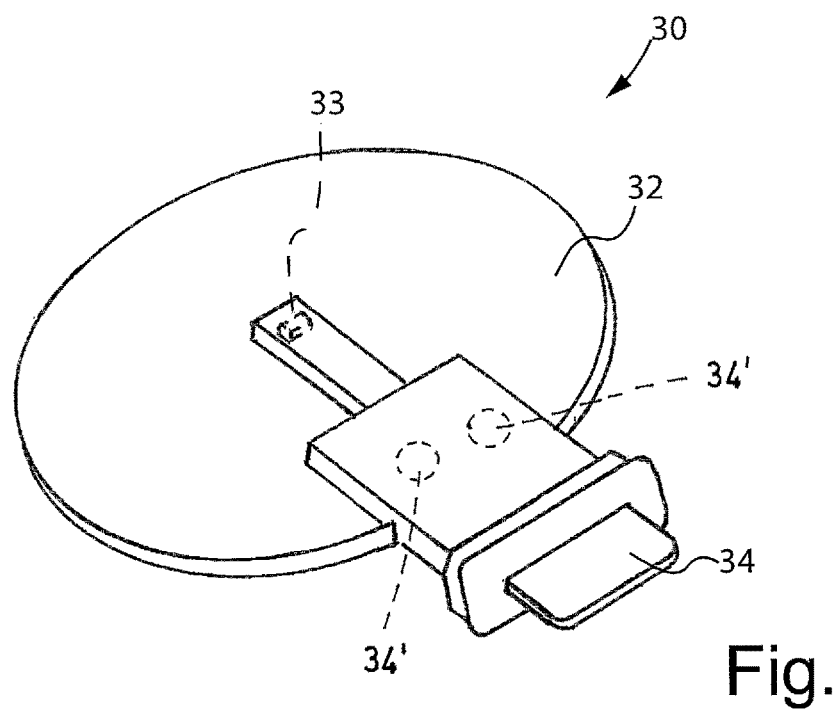
FIG. 3A is a schematic perspective view of a first embodiment of the disposable heating element of the cartridge of FIG. 1.
Figure 4:
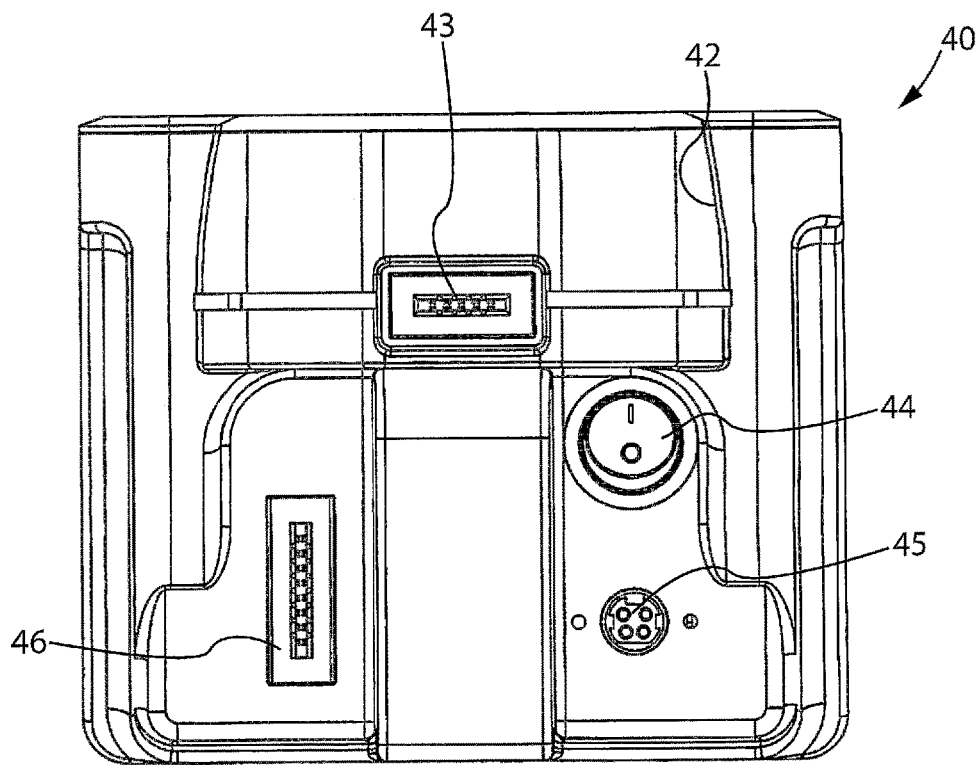
FIG. 4 shows the rear of the control and power supply unit of the cartridge of FIG. 1.
Figure 3B:
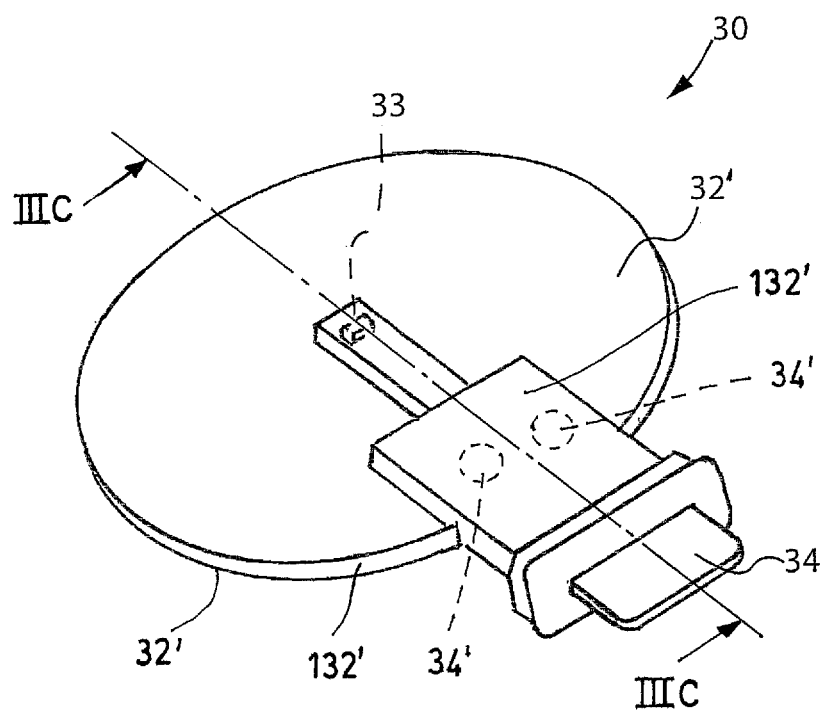
FIG. 3B is a schematic perspective view of a second embodiment of the disposable heating element of the cartridge of FIG. 1.
Figure 3C:
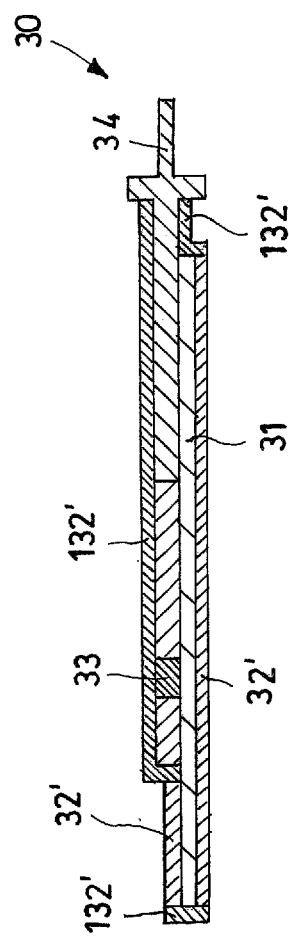
FIG. 3C is a section view of FIG. 3B along a plane of trace IIIC.

Two electrical contacts 34' are provided, schematically shown in FIGS. 3A and 3B, which put the electrical resistor 31 in contact with an electrical connector 34.

According to a preferred embodiment of the invention, the electrical resistor 31 bears an integrated thermistor 33 able to keep monitoring its internal temperature, which must not exceed a predefined value to avoid the degradation of the coating made of medical silicone, and to verify any malfunctions.

The electrical connector 34 for the electrical connection of the resistor 31 contained in the disposable cartridge 20 projects in part from the wall of the chamber 21.

The electrical resistor 31, of appropriate power, assures the attainment of the temperature of the water necessary to supply adequate temperature and humidity to the gases inspired by the patient, also if high constant flows are used.

According to an embodiment of the invention, shown schematically in FIG. 3A, the electrical resistor 31 is overprinted with a film of medical grade silicone 32, which provides a sealed external coating, to avoid the entry of water and to isolate the two electrical contacts 34'.

According to an additional embodiment of the invention, shown schematically in FIG. 3B, the electrical resistor 31, comprising the metallic wire coated with the thin layer of silicone, is coupled with aluminium foils 32', preferably with thickness between 0.1 mm and 0.5 mm.

The aluminium foils 32' are preferably fixed on the thin layer of silicone coating the metallic wire of the electrical resistor 31 for example by vulcanisation, so as to avoid the presence of layers of air between the resistor 31 and the aluminium foils 32', which would disadvantageously act as a heat insulator.

The aluminium foils 32', in the example shown, are two foils, substantially planar and with circular shape, respectively positioned above and below the electrical resistor 31. The lower aluminium foil 32' is planar and circular and the upper aluminium foil 32' is shaped in the plane in a manner adapted to house the connector 34; for example, it is cut around the connector 34, which may integrate the thermistor 33.

Alternatively, according to an embodiment not shown, the upper aluminium foil 32' can be, similarly to the lower aluminium foil 32', circular and so shaped as to form a seat able to house and cover the connector 34 which may integrate the thermistor 33.

On the entire perimetric edge of the resistor 31 and on the two electrical contacts 34' on the connector 34 a layer of sealing material 132' is provided, for example medical silicone, to seal the resistor 31 and avoid the entry of water and to isolate the two electrical contacts.

Figure 3D:
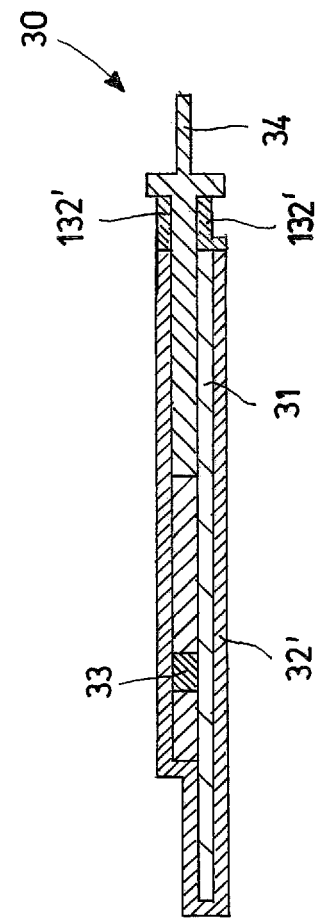
FIG. 3D shows a section view of an additional variant of the disposable heating element according to the invention.
Figure 5:
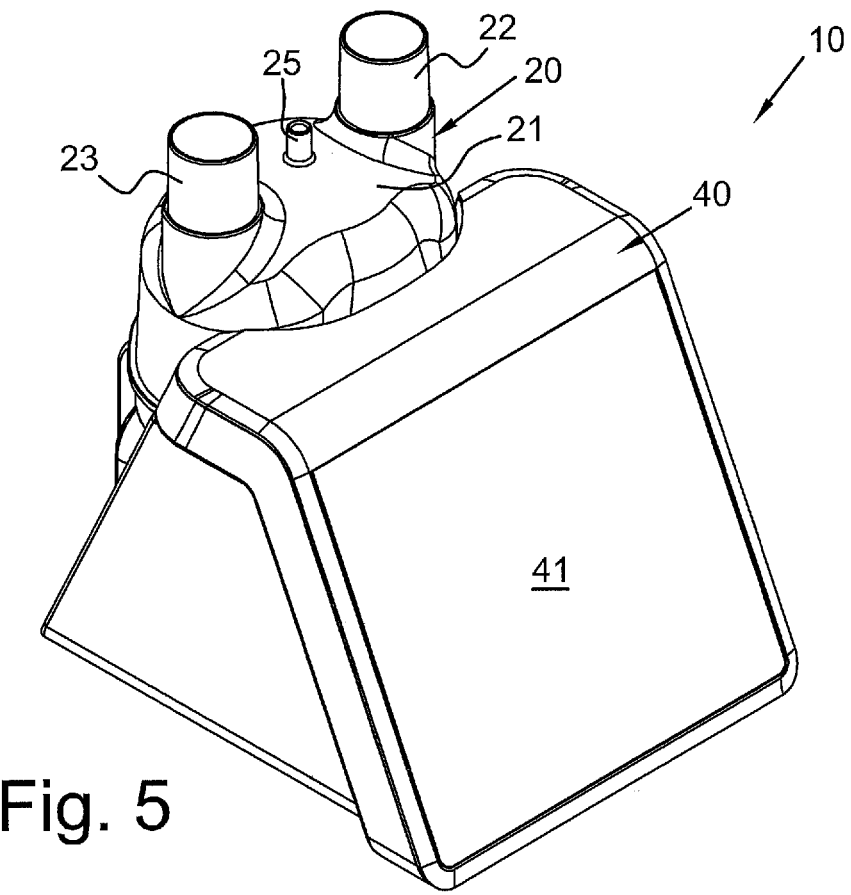
FIGS. 5 and 6 are respectively a front perspective view and a lateral view of the active humidifier according to the invention.
Figure 6:
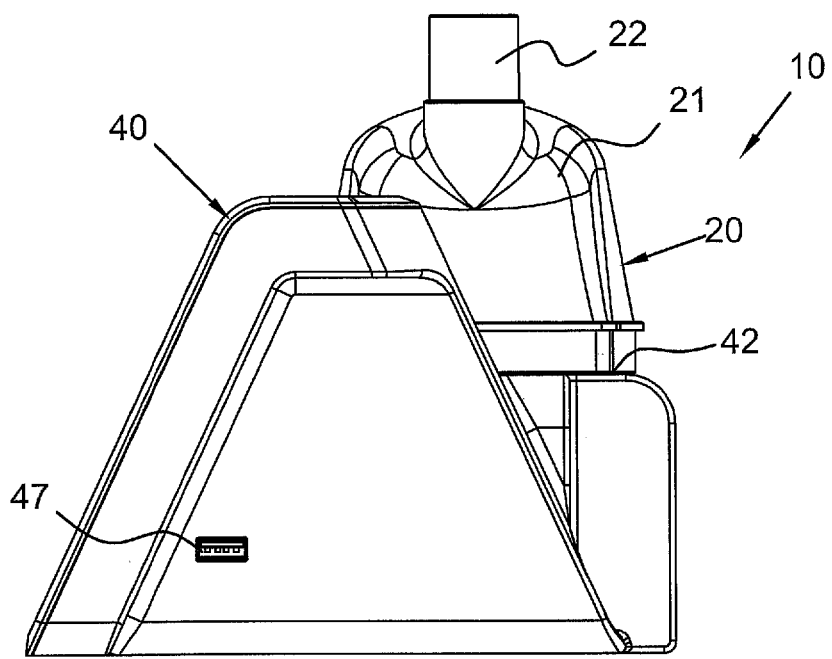

In another example, shown in FIG. 3D, the aluminium in foils 32' could configure a single pocket, obtained by drawing, to house the electrical resistor 31, the inner part of the connector 34 and the thermistor 33. In this configuration it is advantageously superfluous to apply an outer silicone seal, except possibly limited to the inlet portion to the chamber 21.

According to an additional embodiment, not shown, the thermistor 33 and possibly a portion of the connector 34 are embedded inside the electrical resistor 31 itself, i.e. in direct contact with the metallic wire under the thin layer of silicone coating the metallic wire.

The positioning of the thermistor 33 internal to the inner resistor 31, i.e. internal to the thin layer of silicone that coats the metallic wire, allows an even more precise reading of the temperature of the heating element 30 and therefore it makes the heating element 30 more reliable.

The use of aluminium sheets 32' as a coating of the disposable heating element 30 allows a sharply higher heat conduction than the coating with the medical-grade silicone film 32.

In fact, the heat conduction of aluminium is 290·W $m^{-1} \cdot K^{-1}$ versus approximately 0.2 $W \cdot m^{-1} \cdot K^{-1}$ of the silicone used previously.

This allows a better heat conduction between the electrical resistor 31 and the water to be heated, considerably improving the effectiveness of the system, allowing the water to reach higher temperature with lower consumption of electrical power.

This obviously is due to the fact that the water is in direct contact, through the aluminium, with the heating element.

The humidification chamber 21 is a sealed case entirely made of plastic material. In fact, the disposable cartridge 20 according to the invention does not have a metallic outer contact surface.

The level of the water inside the humidification chamber 21 is controlled through a known float, not shown, which effects a hydraulic closure/opening on an inlet hole for the entry of the water 25.

According to the invention, the active humidifier 10 further comprises two capacitive sensors to signal with an audible warning device any attainment of a minimum level and a maximum level of the water present inside the humidification chamber 21 and to signal any alarm in case of erroneous level.

The water contained in the cartridge 20 and in direct contact with the heating element 30 is rapidly heated. The residual volume contained in the disposable cartridge 20 is in turn rapidly heated by the water contained in the cartridge 20. The inspiratory gases that traverse the residual volume of the cartridge 20 are rapidly heated and humidified.

From the above description it is evident that the entire system is based on only four heat conduction steps: disposable electrical resistor—water contained in the disposable cartridge—residual volume of gas in the disposable cartridge—inspiratory gases that traverse the disposable cartridge.

The active humidifier 10 according to the invention comprises a control and power supply unit 40 of the cartridge 20, preferably provided with a user interface panel 41, for displaying and setting the operating parameters of the active humidifier 10.

The control and power supply unit 40 of the cartridge 20 further comprises a housing seat 42 of the cartridge 20, provided with an electrical connector 43 for the electrical connection of the electrical resistor 31, able to house the electrical connector 34 of the cartridge 20.

The control and power supply unit 40 of the cartridge 20 further comprises, according to what is shown, an on/off switch 44, a connector for connection with the electrical grid 45, an additional electrical connector 46 able to house other electrical connectors, for example those for supplying power to the circuit 100, as well as a USB plug 47 for example to update the firmware containing the control programmes of the active humidifier 10 and the download of the operating data.

In the active humidifier 10 according to the invention, the control and power supply unit 40 of the cartridge 20 lacks heating elements, such as a reusable heating electrical resistor or a reusable heating metallic element.

The function of the control and power supply unit 40 of the cartridge 20 is only to regulate the electrical energy necessary to heat the water contained in the disposable cartridge 20. This function, according to an alternative form of the active humidifier 10 of the invention, can be carried out by a system external to the humidifier itself.

The control and power supply unit 40 of the cartridge 20 also has the function of positioning of the disposable cartridge 20. This function, according to an alternative form of the active humidifier 10 of the invention, can be carried out by a dedicated system external to the humidifier itself.

The control and power supply unit 40 of the cartridge 20 also has the function of electrically connecting the reusable electrical resistor 31 positioned inside the disposable cartridge 20. This function, according to an alternative form of the active humidifier 10 of the invention, can be carried out by a dedicated normal separate electrical connection.

According to the present invention, the active humidifier 10 is integrated in the thermoregulated circuit 100 for the ventilation of a patient.

The thermoregulated circuit 100 comprises a first tube 110 for the introduction of air from the ventilation device 11, connected to the air inlet mouth 22 of the cartridge 20. The air that transits through this tube, not conditioned, generally has an ambient temperature between 18° C. and 23° C.

The thermoregulated circuit 100 also comprises an inspiration tube 120 connected at a first end thereof to the conditioned air outlet mouth 23 of the cartridge 20 by means of a first fitting 121 and connected at an opposite end thereof to a respiratory patient interface Y-fitting 130.

The inspiration tube 120 is provided with a wire electrical resistor 123 arranged along its entire longitudinal development and with a first thermistor 124, positioned in proximity to the outlet of the cartridge 20, and a second thermistor 125, positioned in proximity to the connection with the patient, respectively arranged at opposite ends of the inspiration tube 120. The power delivered to the wire resistor 123 is managed by the thermistor 125 positioned in proximity to the connection with the patient.

The thermoregulated circuit 100 further comprises an expiration tube 140, connected at a first end to the respiratory interface Y-fitting 130 and provided with a wire electrical resistor 143 arranged along its entire longitudinal development. The opposite end of the expiration tube 140 is connected to the ventilation device 11. The air expired by the patient into the expiration tube 140 through the Y fitting 130 has a temperature of approximately 34° C. while at the output from the expiration tube 140 it was heated to maintain an equal or higher temperature value.

According to the invention, the respiratory interface Y fitting 130 comprises a connector 131 for the connection and acquisition of a patient temperature probe 132 of a known, standardised type, shown schematically in FIG. 7.

Such temperature probes, which have long been on the market and used daily in critical areas of hospital wards, constantly measure the patient's body temperature. Such probes can be positioned in the oesophagus, in the pulmonary artery, in the bladder or in the eardrum and they are provided with a standardised connector.

The continuous acquisition by the active humidifier 10 of the patient's body temperature through direct connection with a patient temperature probe 132 is used to perform an automatic control of the operation of the active humidifier 10, automatically adapting it to changes in the patient's body temperature, providing ideal inspiratory gases, proportionate to aforesaid temperature changes, improving the patient's respiratory comfort.

Into the first fitting 121 merge, according to the invention, a pair of wires of the electrical resistor 123, a pair of wires for each of the two thermistors 124 and 125 and a pair of wires, not shown in FIG. 7, of the connector 131 of the patient temperature probe 132. A printed circuit board (PCB) connector 122, integrated in the first fitting 121 of the inspiration tube 120, provides for the electrical power supply of the resistor 123, the acquisition of the thermistors 124, 125 and the acquisition of the patient temperature probe 132 associated with the inspiration tube 120.

In particular, the thermistor 124 is placed at the centre of the flow of the inspiratory gases, in the outlet fitting 121 for the outflow of the gases from the cartridge 20.

The welding of the thermistor 124 and of its pair of wires on the PCB connector 122 assures the same positioning of the temperature sensor on each individual thermoregulated circuit 100 produced.

The reading carried out by said thermistor 124 assures the perfect regulation of the power supplied and to be supplied to the electrical resistor 31 positioned inside the humidification chamber 21, in order to maintain constant the value of temperature of the water as the flow of gas that traverses it changes, and consequently the value of temperature of the gases supplied to the patient.

The function of the second thermistor 125 positioned in proximity to the patient connection is to control and modulate the power supplied to the resistor 123 positioned inside the inspiration tube 120. The aim of said resistor 123 is to keep constant and/or to regulate the temperature of the air flowing out of the cartridge 20 and therefore to prevent the formation of condensation inside the inspiration tube 120 which is caused by the temperature drop during the travel from the cartridge 20 to the patient.

The expiration tube 140 is connected at the opposite end to a second fitting 141 connectable to the ventilation device 11.

Into the second fitting 141 merges a pair of wires of the electrical resistor 143, which are supplied with electrical power through a printed circuit board (PCB) connector 142, integrated in the second fitting 141 of the expiration tube 140.

The function of the electrical resistor 143 positioned inside the expiration tube 140 is to prevent the formation of condensation inside this part of the circuit as well. Considering that the temperature of the gases expired by the patient is approximately 34° C., practically constant, it is possible to avoid control on the power of said resistor 143, also considering that heating the air inside the expiration tube 140 at higher values than those inspired does not entail any problem, since the tube is downstream of the patient.

The active humidifier 10 and the related thermoregulated circuit 100 is intended for adult, pediatric and neonatal patients.

The active humidifier 10 and the related thermoregulated circuit 100, according to the invention, is used to assure the humidification of inspiratory gases in intubated patients or in NIV (Non-invasive Ventilation), with both alternating and constant flows through the use of interfaces such as helmets, masks or high flow cannulas and it is advantageously designed to be used in intensive care units and in all hospital and non-hospital environments, including homes.

The active humidifier and the thermoregulated circuit integrating said active humidifier of the present invention has the following advantages:

Greater rate of heating of the inspiratory gases to reach the set value of temperature and humidity even as flows change;

Greater precision of the administrated value of temperature with respect to the set value of temperature;

Greater constancy of the temperatures administered to the patient;

Reduction of the thermal "Pendulum" effect;

Disposable cartridge of smaller dimensions;

Lower electrical power necessary to heat the water contained in the cartridge, both because the system, since the heating element is immersed in the water and hence in direct contact, is faster and more effective, and because the volume of water contained therein is smaller;

Lower consumption of electricity.

Another advantage of the active humidifier and of the thermoregulated circuit according to the invention is the possibility of executing an automatic feedback on the basis of the body temperature of the patient acquired by the system.

In fact, it is well known that the body temperature of a patient can change several times within the same day. To changes in the body temperature of the patient corresponds a different quantity of temperature and humidity released in the expired gases by the patient itself. Therefore, to a change in the body temperature of the patient, corresponds a change in the temperature and humidity expired and hence relinquished/lost.

The ability to condition the inspiratory gases in a manner that is automatic and dependent on the value of the patient's body temperature and of its changes with immediacy offers advantages, for example for the comfort of the patient him/herself and greater practicality for health care operators who are forced to make small temperature changes of the active humidifier as body temperature changes.

The active humidifier and the thermoregulated circuit integrating such active humidifier as conceived herein are susceptible to many modifications and variations, all falling within the invention; furthermore, all the details are replaceable by technically equivalent elements. In practice, the materials used, as well as the dimensions thereof, can be of any type according to the technical requirements.

The invention claimed is:

1. An active humidifier comprising:
    a disposable cartridge provided with a humidification chamber adapted to contain a volume of water and a residual volume of gas to be heated for air humidification of inspiratory gases traversing the disposable cartridge, with an inlet mouth for air to be introduced in the humidification chamber by a ventilation device and with an outlet mouth for conditioned air exiting the humidification chamber to a patient, the humidification chamber being a sealed casing entirely made of plastic material, wherein the disposable cartridge comprises a disposable heating element comprising an electrical resistor, the disposable cartridge also comprising an electrical connector for electrical connection of the disposable heating element, wherein the disposable heating element is positioned on a plurality of support pegs, which keeps the disposable heating element distanced from a bottom inside of the humidification chamber, immersed in the water and lapped on all sides by the water.

2. The active humidifier according to claim 1, wherein said disposable heating element has planar development substantially equal to a diameter of the humidification chamber.

3. The active humidifier according to claim 1, wherein said electrical resistor is coupled to aluminium foils.

4. The active humidifier according to claim 3, wherein said aluminium foils are two substantially planar foils with circular shape positioned respectively above and below the electrical resistor, a layer of sealing material made of medical silicone being provided on a perimetric edge of the electrical resistor between the two aluminium foils the two aluminium foils comprise a lower aluminium foil and an upper aluminium foil wherein the lower aluminium foil is planar and circular and the upper aluminium foil is adapted to house the electrical connector.

5. The active humidifier according to claim 4, wherein a layer of sealing material of medical silicone is also provided on two electrical contacts of the electrical connector.

6. The active humidifier according to claim 3, wherein the aluminium foils are configured to form a single drawn pocket.

7. The active humidifier according to claim 3, wherein the aluminium foils have a thickness between approximately 0.1 mm and 0.5 mm and fixed on the electrical resistor by vulcanisation.

8. The active humidifier according to claim 1, wherein said electrical resistor is coated with a silicone film.

9. The active humidifier according to claim 1, wherein said disposable heating element bears an integrated thermistor for monitoring an internal temperature of the electrical resistor.

10. The active humidifier according to claim 1, further comprising a control and power supply unit of the disposable cartridge, provided with a user interface panel and comprising a housing seat for the disposable cartridge provided with an electrical connector for electrical connection of the disposable cartridge, wherein said control and power supply unit of the disposable cartridge lacks heating elements.

11. A thermoregulated circuit for ventilation of a patient comprising:
a first tube for introducing air from a ventilation device;
a respiratory patient interface Y-fitting;
an inspiration tube, said inspiration tube being provided with a wire electrical resistor arranged along its entire longitudinal development and with a first thermistor and a second thermistor respectively arranged at opposite ends of the inspiration tube;
an expiration tube provided with a wire electrical resistor arranged along its entire longitudinal development; and
the active humidifier according to claim 1,
wherein the first tube is connected to the inlet mouth of the disposable cartridge, the inspiration tube is connected, at a first end thereof, to the outlet mouth of the disposable cartridge by means of a first fitting and connected, at an opposite end thereof, to the respiratory patient interface Y-fitting, the expiration tube is connected at a first end to the respiratory interface Y-fitting.

12. The thermoregulated circuit according to claim 11, wherein the respiratory patient interface Y-fitting comprises a connector for connection of a patient temperature probe.

13. The thermoregulated circuit according to claim 11, wherein said expiration tube is connected at an opposite end to a second fitting connectable to the ventilation device.

14. The thermoregulated circuit according to claim 13, wherein pairs of wires of the wire electrical resistor of the inspiration tube, the first and second thermistors and a connector of a patient temperature probe are power supplied by means of a printed circuit connector integrated in the first fitting of the inspiration tube and that a pair of wires of the wire electrical resistor of the expiration tube is power supplied by means of a printed circuit connector integrated in the second fitting of the expiration tube.

15. The thermoregulated circuit according to claim 14, wherein the first thermistor is placed at a centre of an inspiratory gas flow, in the first fitting positioned at the outlet mouth of the disposable cartridge.

* * * * *